US009944993B2

(12) United States Patent
Xu et al.

(10) Patent No.: US 9,944,993 B2
(45) Date of Patent: Apr. 17, 2018

(54) METHOD FOR ENRICHMENT OF CIRCULATING TUMOR DNA AND REAGENT FOR ENRICHMENT OF CIRCULATING TUMOR DNA

(71) Applicant: HAPLOX BIOTECHNOLOGY(SHENZHEN) CO., LTD., Shenzhen (CN)

(72) Inventors: Mingyan Xu, Shenzhen (CN); Xiaoni Zhang, Shenzhen (CN)

(73) Assignee: Haplox Biotechnology (Shenzhen) Co., Ltd., Nanshan District, Shenzhen, Guangdong (CN)

( * ) Notice: Subject to any disclaimer, the term of this patent is extended or adjusted under 35 U.S.C. 154(b) by 0 days.

(21) Appl. No.: 15/127,736

(22) PCT Filed: Jan. 6, 2015

(86) PCT No.: PCT/CN2015/070188
§ 371 (c)(1),
(2) Date: Sep. 20, 2016

(87) PCT Pub. No.: WO2016/109939
PCT Pub. Date: Jul. 14, 2016

(65) Prior Publication Data
US 2017/0067117 A1 Mar. 9, 2017

(51) Int. Cl.
*C12P 19/34* (2006.01)
*C12Q 1/68* (2018.01)

(52) U.S. Cl.
CPC ........... *C12Q 1/6886* (2013.01); *C12Q 1/686* (2013.01); *C12Q 1/6806* (2013.01); *C12Q 2600/158* (2013.01)

(58) Field of Classification Search
USPC ................................................ 435/6.12, 91.2
See application file for complete search history.

(56) References Cited

U.S. PATENT DOCUMENTS

| | | | |
|---|---|---|---|
| 2012/0302448 A1* | 11/2012 | Hutchison | C12Q 1/686 506/2 |
| 2013/0189684 A1* | 7/2013 | Ehrich | C12Q 1/6886 435/6.11 |
| 2014/0256558 A1* | 9/2014 | Varley | C12Q 1/6853 506/2 |
| 2014/0274740 A1* | 9/2014 | Srinivasan | C12Q 1/6806 506/2 |
| 2015/0133391 A1* | 5/2015 | de Vlaminick | C12Q 1/689 514/20.5 |
| 2015/0284783 A1* | 10/2015 | Canton | C12Q 1/6825 435/6.11 |

FOREIGN PATENT DOCUMENTS

| | | |
|---|---|---|
| CN | 104212879 A | 12/2014 |
| WO | 2014028378 A2 | 2/2014 |

OTHER PUBLICATIONS

PCT Written Opinion for PCT/CN2015/070188 dated Oct. 10, 2015 and its English translation.
Bu Zhao-de, Xue Zhong-qi, Lin Ben-yao, et al., "The divergence among physical palpation, mammography and ultrasonography in measuring the size of breast tumor", Chinese Journal of Clinical Oncology and Rehabilitation, vol. 7(1), pp. 39-41 (3 pages), 2000 with Machine English translation by Google Translate.
Hideharu Kimura, Kazuo Kasahara, Kazuhiko Shibata, et al., "EGFR Mutation of Tumor and Serum in Gefitinib-Treated Patients with Chemotherapy-Naive Non-small Cell Lung Cancer", Journal of Thoracic Oncology, vol. 1(3), pp. 260-267, Mar. 2006.
Jae Jin Lee, Chi Hoon Maeng, Seon Kyung Baek, et al., "The immunohistochemical overexpression of ribonucleotide reductase regulatory subunit M1 (RRM1) protein is a predictor of shorter survival to gemcitabine-based chemotherapy in advanced non-small cell lung cancer (NSCLC)", Lung Cancer, vol. 70, pp. 205-210, 2010.
S. A. Leon, B. Shapiro, D. M. Sklaroff, and M. J. Yaros, "Free DNA in the Serum of Cancer Patients and the Effect of Therapy", Cancer Research, vol. 37, pp. 646-650, Mar. 1977.
Tony S. Mok, Yi-Long Wu, Sumitra Thongprasert, et al., "Gefitinib or Carboplatin-Paclitaxel in Pulmonary Adenocarcinoma", The New England Journal of Medicine, vol. 361(10), pp. 947-957, Sep. 3, 2009.
K Tamura, I Okamoto, T Kashii, et al., "Multicentre prospective phase II trial of gefitinib for advanced non-small cell lung cancer with epidermal growth factor receptor mutations: results of the West Japan Thoracic Oncology Group trial (WJTOG0403)", British Journal of Cancer, vol. 98, pp. 907-914, Feb. 19, 2008.

(Continued)

*Primary Examiner* — Kenneth R Horlick
(74) *Attorney, Agent, or Firm* — Ladas & Parry, LLP (57) ABSTRACT

The present invention provides a method and a reagent for enrichment of circulating tumor DNA, the method comprising the steps of mixing a water phase and an oil phase and shaking the mixture to prepare an emulsion PCR reaction system, and performing emulsion PCR amplification, wherein the water phase comprises peripheral blood plasma DNA as template DNA, a forward primer and a reverse primer, dNTPs, a PCR buffer and a DNA polymerase, the peripheral blood plasma DNA having adapter sequences connected to both ends thereof, and the forward primer and the reverse primer being complementary to the adapter sequences at the two ends respectively; separating the water phase from the oil phase following the emulsion PCR amplification to obtain a PCR amplification product in the water phase; and capturing circulating tumor DNA in the PCR amplification product in the water phase by using a probe sequence that specifically binds to the circulating tumor DNA. The method of the present invention is capable of performing single-molecule high-fidelity ultramicro parallel amplification and effectively capturing peripheral blood plasma ctDNA to provide adequate amount of ctDNA to be used for subsequent sequencing detection.

18 Claims, 3 Drawing Sheets

(56) References Cited

OTHER PUBLICATIONS

International Search Report for PCT/CN2015/070188 dated Oct. 10, 2015 and its English translation provided by WIPO.
International Search Report for PCT/CN2015/070188 dated Oct. 10, 2015 and its English translation.

* cited by examiner

METHOD FOR ENRICHMENT OF CIRCULATING TUMOR DNA AND REAGENT FOR ENRICHMENT OF CIRCULATING TUMOR DNA

CROSS-REFERENCE TO RELATED APPLICATION

This application is the U.S. National Stage of International Patent Application No. PCT/CN2015/070188 filed on Jan. 6, 2015, the disclosure of which is hereby incorporated by reference in its entirety.

TECHNICAL FIELD

The present invention relates to the technical field of PCR (polymerase chain reaction) ultramicro parallel amplification, in particular to a method and a reagent for enrichment of circulating tumor DNA.

BACKGROUND OF THE INVENTION

Since 2003, as the Human Genome Project develops, the first generation sequencing (Sanger) and the second generation sequencing (NGS) techniques have been gradually occupying the molecular diagnostics market due to their sensitivity and accuracy. Genomics at the molecular level has also become a research hotspot in biological sciences for the $21^{st}$ century. The emerging clinical application of gene sequencing technologies, the discovery of various cancer-related genes and the advancement of the Cancer Genome Project represent the dawn of early diagnosis, personalized therapy and prognosis of cancers. Currently, genomic DNA is primarily obtained from tissue cells by such processes as extraction following disruption of live tissue cells and in vitro PCR amplification from paraffin specimen of tissue cells. However, there still exists a technical barrier as to how to diagnose the onset of cancers and even prevent them at DNA level for early-stage patients.

The data obtained about the survival rate against malignancies provides important information that reflects tumor burden in a region and that can be used to evaluate the medical resources as well as the level of prevention and treatment in the region. An analysis of cancer survival rate during 2003 to 2005 conducted by National Center for Cancer Registries revealed that five-year relative survival rate was only 30.9% in our country. The survival rates for major cancers were 16.1% for lung cancer, 27.4% for stomach cancer, 10.1% for liver cancer, 20.9% for esophagus cancer, 47.2% for colorectal cancer, and 73% for breast cancer, respectively. The cancer survival rates differ significantly between urban and rural areas. While in developed countries, the five-year survival rates for colorectal cancer and breast cancer reached 60% and 85% respectively, and the rates for liver cancer and lung cancer with poor prognosis reached 15 to 20%, higher than in our country (data from Lancet). It is evident that "three earlies", i.e., early discovery, early diagnosis and early treatment are required in order to raise the five-year survival rates of cancer patients in our country.

The means currently clinically used for diagnosing and evaluating cancers mainly involves a combination of localization by imaging and qualification by tumor markers. Imaging techniques include X ray (chest fluoroscopy, chest X-ray film, low dose CT), magnetic resonance imaging (MIR), radioactive substance (nuclide bone scanning), and PET-CX ray as a conventional means of screening is mainly used for determining the size and the position of a tumor. It needs to be used in combination with detection of tumor markers to achieve a definite diagnosis. MIR detects whether there exists tumor metastasis to the brain or the spinal cord, and nuclide bone scanning detects whether there exists tumor metastasis to bones. Both detection techniques are mainly used for diagnosing post-phase III tumors. PET (positron emission computed tomography), characterized by being non-traumatic, is at present the only technique for imaging function, metabolism and receptors in the manner of anatomical morphology. PET-CT, as a combination of PET and CT techniques for screening for tumor location and metastasis, is one of the best means clinically used for diagnosing tumors and guiding the treatment of same. However, such diagnosis methods are relatively costly and are not covered by medical insurances. Many patients have to abandon the use of these methods because they are unable to afford the expensive diagnostic fee. Imaging detection is mainly used for localizing malignancies. In order to define the type and the phase of a cancer, it is necessary to further evaluate tumor markers, whereby the cancer can be identified or diagnosed according to the biochemical or immunological characteristics of the tumor markers. A tumor marker is a substance produced and released by a tumor cell, and is generally present in the tumor cell or in the body fluid of the host in the form of a metabolic product such as antigen, enzyme, hormone etc. Tumor markers useful in clinical detection are alpha-fetal protein (AFP), carcinoembryonic antigen (CEA), carbohydrate antigen family (CA125, CA15-3 etc.), among others.

However, at stages when cancers are definitely diagnosed, the malignancies detectable by the clinically used conventional imaging techniques described above have a diameter of 1 cm or more, a tumor cell number on the order of $10^9$, and a weight of more than 1 g. Despite its high sensitivity, PET-CT technique can only detect tumors larger than 0.5 cm or more (H. Li et al. 2013; Bu Zhaode, Xue Zhongqi et al., 2000). That is, tumor patients diagnosed by imaging techniques are mostly at the middle or late stage, and have already missed the optimal period of cancer treatment. At the early stage of a cancer, even if tumor markers are detected, the particular position of the tumor tissue cannot be identified by imaging detection and the tumor cannot be ultimately definitely diagnosed. Therefore the cancer cannot be treated, and can only be left to develop and worsen.

Drug resistance of tumors and recurrence after cure are among the most important reasons responsible for the death of tumor patients. Addressing these two problems has become a research hotspot in tumor diseases now in the world. Presently, there lacks an effective means for the evaluation of drug administration during clinical cancer treatment. Taking lung cancer as an example, gefitinib (Iressa) and Erlotinib (Tarceva) are drugs for treating non-small cell lung cancer (NSCLC), but clinical data suggested that such drugs are not suitable for use with all patients of non-small cell lung cancer. Further investigations found that patients with EGFR (epidermal growth factor receptor) mutation were more responsive to treatment with Iressa by 40% or higher than non-selective patients (Tony S. Mok, M. D. et al., 2009; Hida T, Okamoto I, Kashii T, et al., 2008; Kimura H, Kasahara K, Kawaishi M, et al., 2006). Gemcitabine is a difluoronucleoside antimetabolite anti-cancer drug that disrupts cell replication. It is suitable for treating non-small cell lung cancer at the middle and late stages. Researches indicated that patients with a low expression of RRM1 (RRM1 gene is mapped on the short arm of chromosome 1 and encodes ribonucleotide reductase M1 subunit) exhibited a control rate of the disease of 30% or higher when treated with gemcitabine (Lee et al., 2010). European Medicines Agency definitely specifies that patients with non-small cell lung cancer must be detected for EGFR gene before using Iressa, and patients with metastatic large intestine cancer must be detected for KRAS gene before using the targeting drugs Erbitux and Vectibix (see the official website of European Medicines Agency http://www.ema.europa.eu/ema/). It is evident that for the treatment of malignancies, guidance and evaluation of drug administration is an important precondition and basis for optimizing therapeutic regimens and achieving effective treatment. Studies on tumor onset and development by systems biology concluded that DNA mutation or genetically-acquired defective genes are key to the development of drug resistance. Therefore it is a general trend to provide, at gene level, personalized guidance and evaluation of drug administration.

In addition to the above, there exists a blind period of detection in the prognosis of clinical treatment of cancer. For example, many cancer patients have their tumor tissues removed by surgery to prevent the tissues from metastasizing and endangering their lives. After the surgery, they need to receive regular biopsy reexamination for prognostic evaluation. Due to the considerable radiation in imaging detection that does harm to human body, the cancer patients mostly receive reexamination post surgery on a yearly basis, which greatly affects the timeliness of prognostic evaluation. This suggests that there is an urgent need in the cancer diagnosis field for a more convenient and non-traumatic detection technique. In a word, the screening, diagnosis, treatment and prognosis of early-stage cancers in current clinical medicine would be a major breakthrough in cancer treatment, and would be key to increasing the five-year survival rates against the cancers. There are substantial technical problems in this field that confronts both medical research and clinical application activities.

In 1947, Mandel and Metais discovered an extracellular DNA in body fluid such as blood, synovial fluid and cerebrospinal fluid, which mainly exists in the form of a DNA-protein complex or a free DNA (Mandel and Metais, 1947). In the 1980's, Leon et al. found that the DNA level in the peripheral serum of tumor pateints was considerably higher than that in normal people (Leon et al., 1977). Moreover, researches revealed that cancer gene mutations consistent with primary tumors were detected in the plasma and serum of patients with the tumors. This suggests that circulating DNA as a novel tumor maker would play an important role in the diagnosis, treatment and prognosis of tumors. Circulating tumor DNA (ctDNA) is a DNA that is released into the circulation system after it comes off of a tumor cell or after apoptosis of the cell, and, as such, can be qualified, quantitated and traced. Successful capture of ctDNA and accurate interpretation of the information contained therein would provide an exact means for acquisition of gene information of early-stage cancers, early diagnosis and prognostic detection of the cancers, and evaluation of drug resistance.

However, such techniques are not effectively developed and widely used for the time being. One of the reasons is that ctDNA is present in the peripheral blood in a very low amount, and in particular, its relative content is extremely low in comparison to normal DNA (nDNA). It is still difficult for current detection technologies to directly detect the ctDNA level in peripheral blood. Therefore, a need exists to enrich target ctDNA by using a DNA enriching process prior to sequencing the enriched ctDNA to obtain the information contained therein and ascertain the diseased state of a subject according to the information obtained from sequencing.

SUMMARY OF THE INVENTION

The present invention provides a method and a reagent for enrichment of circulating tumor DNA. The method is capable of performing single-molecule high-fidelity ultra-micro parallel amplification and effectively capturing peripheral blood plasma ctDNA to provide adequate amount of ctDNA to be used for subsequent sequencing detection.

According to a first aspect, the present invention provides a method for enrichment of circulating tumor DNA, comprising the steps of:

single-molecule parallel amplification:mixing a water phase and an oil phase and shaking the mixture to prepare an emulsion PCR reaction system, and performing emulsion PCR amplification, wherein the water phase comprises peripheral blood plasma DNA as template DNA, a forward primer and a reverse primer, dNTPs, a PCR buffer and a DNA polymerase, the peripheral blood plasma DNA having adapter sequences connected to both ends thereof, and the forward primer and the reverse primer being complementary to the adapter sequences at the two ends respectively;

separation of the water phase and the oil phase: separating the water phase from the oil phase following the emulsion PCR amplification to obtain a PCR amplification product in the water phase; and capture of circulating tumor DNA:capturing circulating tumor DNA in the PCR amplification product in the water phase by using a probe sequence that specifically binds to the circulating tumor DNA.

In a preferred embodiment of the present invention, the water phase of the emulsion PCR reaction system further comprises dUTP.

Preferably, the dUTP and the dNTPs are in a molar ratio of from 1:1000 to 1:10, more preferably 1:100.

In a preferred embodiment of the present invention, the adapter sequences are sequencing adapter sequences used in a sequencer.

Preferably, the sequencer is an Illumina sequencer, and the forward primer and the reverse primer to which the sequencing adapter sequences correspond are 5'-TCCCTA-CACGACGCTCTTCCGATCT-3' (SEQ ID NO: 1) and 5'-TGAACCTGAACCGCTCTTCCGATCT-3' (SEQ ID NO: 2) respectively.

Preferably, the sequencer is a Life Tech sequencer, and the forward primer and the reverse primer to which the sequencing adapter sequences correspond are 5'-CCATCTCATC-CCTGCGTGTCTCCGA-3' (SEQ ID NO: 3) and 5'-CCGCTTTCCTCTCTATGGGCAGTCG-3' (SEQ ID NO: 4) respectively. In a preferred embodiment of the present invention, the water phase and the oil phase is in a volume ratio of from 1:10 to 1:1, preferably from 1:5 to 1:2.

In a preferred embodiment of the present invention, the DNA polymerase is a high-fidelity DNA polymerase, preferably a high-fidelity Klenow Fragment (DNA polymerase I), a KAPA HiFi family high-fidelity DNA polymerase, a Phusion family high-fidelity DNA polymerase or a Q5 family high-fidelity DNA polymerase.

In a preferred embodiment of the present invention, in the water phase, the peripheral blood plasma DNA is in a total amount of from 1 to 100 ng, the forward primer and the reverse primers are in a final concentration of from 0.1 to 1 µM, the dNTPs are in a final concentration of from 0.5 to 2 mM, the PCR buffer is in a final concentration of 1×, and the DNA polymerase is in a final concentration of from 0.1 to 1 U.

More preferably, in the water phase, the peripheral blood plasma DNA is in a total amount of from 1 to 10 ng, the forward primer and the reverse primers are in a final concentration of 0.5 μM, the dNTPs are in a final concentration of 1 mM, the PCR buffer is in a final concentration of 1×, and the DNA polymerase is in a final concentration of 0.25 U.

Preferably, the procedure of the emulsion PCR amplification is as follows: 93-95° C. 1-3 min; 93-95° C. 5-20 s, 61-65° C. 10-20 s, 71-73° C. 5-20 s, 40-60 cycles; and 71-73° C. 4-10 min.

More preferably, the procedure of the emulsion PCR amplification is as follows: 94° C. 2 min; 94° C. 10 s, 63° C. 15 s, 72° C. 10 s, 50 cycles; and 72° C. 5 min.

In a preferred embodiment of the present invention, the probe sequence used in the step of capture of circulating tumor DNA that specifically binds to the circulating tumor DNA comprises biotin modification. After the probe sequence specifically binds to the circulating tumor DNA, the circulating tumor DNA is captured through specific binding of streptavidin magnetic beads with the biotin. It should be noted that the biotin modification can occur at any position in the probe sequence, such as the 5' end, 3' end or any base positions therebetween in the probe sequence.

Preferably, in capturing the circulating tumor DNA by using the probe sequence, the adapter sequences are blocked using blocking sequences, wherein the blocking sequences specifically bind to the adapter sequences at both ends of the peripheral blood plasma DNA.

In a preferred embodiment of the present invention, the step of capture of circulating tumor DNA is particularly achieved by performing PCR amplification using the probe sequence that specifically binds to the circulating tumor DNA as a primer, wherein the probe sequence as a primer is a sequence that specifically binds to the circulating tumor DNA.

In a second aspect, the present invention provides a reagent for enrichment of circulating tumor DNA, comprising the following components:

component for emulsion PCR amplification, which comprises a water phase and an oil phase, wherein the water phase comprises a forward primer and a reverse primer, dNTPs, a PCR buffer and a DNA polymerase, the forward primer and the reverse primer being respectively complementary to the adapter sequences connected to both ends of peripheral blood plasma DNA; and component for capture of circulating tumor DNA, which comprises a probe sequence that specifically binds to the circulating tumor DNA, useful for capturing the circulating tumor DNA in the PCR amplification product in the water phase.

Preferably, the water phase of the emulsion PCR amplification component further comprises dUTP.

Preferably, the dUTP and the dNTPs are in a molar ratio of from 1:1000 to 1:10, more preferably 1:100.

Preferably, the DNA polymerase is a high-fidelity DNA polymerase, preferably a high-fidelity Klenow Fragment (DNA polymerase I), a KAPA HiFi family high-fidelity DNA polymerase, a Phusion family high-fidelity DNA polymerase or a Q5 family high-fidelity DNA polymerase.

In a preferred embodiment of the present invention, the probe sequence comprises biotin modification, and the reagent further comprises streptavidin magnetic beads. After the probe sequence specifically binds to the circulating tumor DNA, the circulating tumor DNA is captured through specific binding of the streptavidin magnetic beads with the biotin.

Preferably, the reagent further comprises blocking sequences that specifically bind to the adaptor sequences at both ends of the peripheral blood plasma DNA, useful for blocking the adaptor sequences when using the probe sequence to capture the circulating tumor DNA.

Preferably, the probe sequence is a sequence that specifically binds to the circulating tumor DNA, useful for performing PCR amplification to obtain enriched circulating tumor DNA.

The method of the present invention, through a combination of emulsion PCR technique and probe capture technique, achieves single-molecule high-fidelity ultramicro parallel amplification and effective capture of peripheral blood plasma ctDNA to provide adequate amount of ctDNA to be used for subsequent sequencing detection. In comparison to conventional pathological detection methods, the method of the present invention does not entail biopsy sampling of tissue cells, but only needs a small amount of peripheral blood plasma to enrich a large amount of ctDNA to be used for subsequent sequencing detection, thus achieving non-traumatic detection. This not only saves detection cost and enhances diagnosis accuracy, but also makes a breakthrough in the detection limits for cancers, achieving early-stage diagnosis in comparison to conventional middle- or late-stage detection. Moreover, the method of the present invention is simple and convenient for use.

It should be noted that the method of the present invention for enrichment of circulating tumor DNA is itself still unable to ascertain whether a subject is afflicted with a cancer, because the method per se only achieves enrichment of circulating tumor DNA in peripheral blood plasma to provide adequate specimen material for analyzing the information contained in the DNA in subsequent sequencing. Therefore, the method for enrichment of circulating tumor DNA cannot itself serve as a diagnostic method.

DETAILED DESCRIPTION OF THE INVENTION

The present invention is described below in further detail by way of embodiments and examples. Unless particularly specified otherwise, the techniques used in the embodiments and examples hereinbelow are all conventional ones known to a person skilled in the art, and the equipments, devices and reagents used are all obtainable, for example commercially available, to a person skilled in the art through public channels.

The present invention mainly addresses the following two problems.

1. The problem of parallel amplification of ctDNA and nDNA. As the ratio of ctDNA to nDNA is about 1:1000, therefore how to effectively achieve parallel amplification is key to the result of judgment. Conventional PCR amplification methods result in the proportion of nDNA becoming larger and larger while that of ctDNA becoming smaller and smaller as amplification proceeds. In the method according to the present invention, the DNA in peripheral blood plasma (including ctDNA and nDNA) is subjected to ultramicro parallel amplification such that the ratio of both DNAs is still 1:1000 after amplification.

2. The problem of capture of ctDNA. As the DNA obtained from the above-said parallel amplification include ctDNA and nDNA, it is necessary to capture the cancer gene fraction from the whole genome to obtain ctDNA. The method of the present invention successfully achieves capture and enrichment of ctDNA through a probe sequence that captures ctDNA.

The method of the present invention can effectively perform single-molecule high-fidelity amplification and capture ctDNA, affording an adequate amount of ctDNA for subsequent detection. The method of the present invention mainly includes two parts, which respectively provide solutions to the two problems mentioned above.

Part one involves a solution to the first problem: performing single-molecule parallel amplification of ctDNA and nDNA by using emulsion PCR (ePCR).

The second part involves a solution to the second problem: capturing and isolating a cancer gene by hybridizing a biotin-labeled oligonucleotide (biotin-oligo) with the cancer gene followed by binding the hybrid to streptavidin magnetic beads; or by designing primers and amplifying ctDNA by PCR.

The specific technical solutions of the present invention are described in two parts as follows.

Part One: Emulsion PCR

Figure 1:
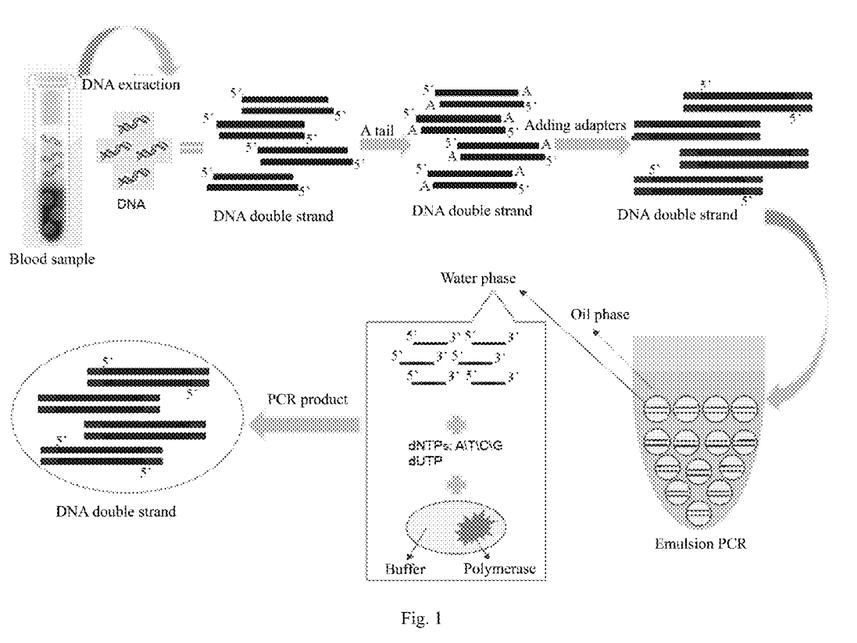
FIG. 1 is a schematic diagram showing the principle and process of the emulsion PCR according to the present invention.

With reference to FIG. 1, emulsion PCR (ePCR) involves PCR amplification using microdroplets in a water-in-oil emulsion system as reactors. The ePCR system includes a reaction system of an oil phase and a water phase. The oil phase serves as a carrier. While there is no limitation on the oil phase used in the present invention, the oil phase systems shown in Table 1 can preferably be used.

TABLE 1

Oil phase systems that can be preferably used in the present inventio

| Oil phase | Formulation |
|---|---|
| 1 | 545 µL of light paraffin oil, 450 µL of 10% Span80 (dissolved in light paraffin oil), 4 µL of Tween80 and 0.5 µL of TritonX-100 |
| 2 | 40% (W/W) silicone oil AR20, 30% (W/W) cyclomethylsiloxane (and) silicone polyol copolymer, and 30% (W/W) film-forming resin 749 FLUID |
| 3 | 7% (W/V) emulsifier ABIL WE90, 20% (V/V) paraffin oil, and 73% (V/V) diethylhexyl carbonate (Tegosoft DEC) |
| 4 | 7% (W/V) emulsifier ABIL WE90 (dissolved in paraffin oil) |

The water-phase reaction system comprises DNA template, dNTPs (including dATP, dTTP, dCTP and dGTP), PCR buffer, DNA polymerase and double distilled water (ddH$_2$O). The DNA template is selected from peripheral blood plasma DNA, which includes double-stranded ctDNA and nDNA. Before performing ePCR, the DNA double strand is modified in three steps. In the first step, the ends of the double-stranded DNA are repaired; in the second step, "A" is added to the 3' end of the DNA fragment; and in the third step, specific adapters are added to the ends of the DNA, which are useful for subsequent sequencing. The choice of the adapters is dependent on the particular sequencer used (common sequencers are available from Illumina and Life Tech etc.).

Research found that addition of a small amount of dUTP in the water-phase system facilitates the reaction, the molar ratio of dUTP to dNTPs preferably being 1:1000 to 1:10, more preferably 1:100.

When an Illumina sequencer is used, part of the sequences of the primers for the adapters is as follows:

```
                                        (SEQ ID NO: 1)
Forward primer (5'-3'): TCCCTACACGACGCTCTTCCGATCT;

(SEQ ID NO: 2)
reverse primer (5'-3'): TGAACCTGAACCGCTCTTCCGATCT.
```

When a Life Tech sequencer is used, part of the sequences of the primers for the adapters is as follows Ion_A (Red, 5'-3'): CCATCTCATCCCTGCGTGTCTC-CGA (SEQ ID NO: 3); Ion_P1 (Blue, 5'-3'): CCGCTTTC-CTCTCTATGGGCAGTCG (SEQ ID NO: 4). Besides, other components in the water-phase reaction system such as dNTPs, dUTP, buffer and DNA polymerase can be prepared into a Master Mix in advance (see Table 2), which is then dispensed in portions and stored at −20° C. for later use.

TABLE 2

Proportions of Components for Preparing a Master Mix (total volume 200 µL)

| Reagent | Quantity | Final conc. (/µL) |
|---|---|---|
| 10× buffer (containing Mg$^{2+}$) | 20 µL | 1× |
| phi29 polymerase (10 U/µL) | 5 µL | 0.25 U |
| dNTPs (10 mM) | 20 µL | 1.0 mM |
| dUTP (0.1 mM) | 20 µL | 10 µM |
| ddH$_2$O | 135 µL | — |

In ePCR, the water phase and the oil phase can be selected in different ratios, for example, 75 µL:400 µL, 240 µL:960 µL, 200 µL:400 µL, and 300 µL:400 µL etc. Taking a ratio of 200 µL:400 µL of the water phase to the oil phase as an example, formulation 2 is selected as the oil phase, and the 400 µL of the oil phase includes 160 µL of silicone oil AR20, 120 µL of cyclomethylsiloxane (and) silicone polyol copolymer (5225C Formulation Aid) and 120 µL of 749 Fluid The water-phase ePCR system and the PCR cycle parameters are as shown in Table 3 and Table 4.

TABLE 3

Proportions of components of the PCR system

| Reagent | Quantity |
|---|---|
| Master Mix | 199 µL |
| DNA template | 1 µL (≥1 ng) |
| ddH$_2$O | Making up to 200 µL |

TABLE 4

PCR cycle parameters

| Step | Temperature | Duration | Cycle times |
| --- | --- | --- | --- |
| Pre-denaturation | 94° C. | 2 min | 1 |
| Denaturation | 94° C. | 10 sec | 50 |
| Primer annealing | 63° C. | 15 sec | |
| Elongation | 72° C. | 10 sec | |
| Final Elongation | 72° C. | 5 min | 1 |
| Cooling | 4° C. | Holding | 1 |

The water phase and the oil phase are sequentially added into a 1.5 mL non-stick reaction tube. After mixing the two phases, the reaction tube containing the reaction system is placed in a tissue lyser (Qiagen Tissue Lyser II) and shaken for 90 seconds at a parameter setting of 13 Hz. The reaction tube is removed, and the oil/water system is dispensed into PCR reaction tubes to perform PCR reaction according to the parameters set forth in Table 4.

Then, after PCR ends, the water phase and the oil phase in the PCR reaction tube are separated. Three processes of separation can be used in the present invention. In the first process, the oil phase in the upper part of the reaction tube is discarded, and 400 µL of paraffin oil is added into the reaction tube. The solution in the tube is vortexed or repeatedly pipetted until the emulsion spheres of the water phase are disrupted and the water phase and the oil phase are sufficiently mixed. The liquid mixed to homogeneity is transferred from the PCR reaction tube to a new non-stick reaction tube. The PCR reaction tube is rinsed with 400 µL of silicone oil, and the rinsed solution is added to the water phase/oil phase mixed solution. The resulting mixture is sufficiently vortexed and centrifuged at 15,000 rpm for 2 minutes, and the upper oil phase is discardedNext, the mixed solution needs to be rinsed with silicone oil for three times. Five hundred (500) µL of silicone oil is added, the resulting mixture is sufficiently vortexed and centrifuged at 15,000 rpm for 1 minutes, and the upper oil phase is discarded. The same procedure is repeated twice to obtain the PCR reaction product in the water phase. In the second process, the water phase and the oil phase in the reaction tube are collected and centrifuged at 9,000 g for 5 minutes. The oil phase is discarded, with the water phase being settled at the bottom of the reaction tube in the form of emulsion spheres. Four hundred (400) µL (2× volume) of saturated ethyl ether is added, the mixture is sufficiently vortexed and centrifuged at 15,000 rpm for 2 minutes, and the upper ethyl ether is discarded. This rinsing with ethyl ether is repeated once to obtain the PCR reaction product in the water phase. In the third process, the water phase and the oil phase in the reaction tube are collected and centrifuged at 15,000 rpm for 10 minutes, and the upper oil phase is discarded. Four hundred 400 µL (2× volume) of phenol/trichloromethane is added, the mixture is sufficiently vortexed and centrifuged at 15,000 rpm for 2 minutes, and the upper phenol/trichloromethane is discarded. This rinsing with phenol/trichloromethane is repeated once to obtain the PCR reaction product in the water phase.

As the PCR polymerase, generally selected are high-fidelity Klenow Fragment (DNA Polymerase I), KAPA HiFi family DNA polymerase, high-fidelity Phusion family DNA polymerase and high-fidelity Q5 family DNA polymerase, among others. It is to be noted that the DNA product obtained is a single-stranded DNA containing adapters at both ends. In order to avoid the incorporation of nDNA due to complementarity to the adapters on DNA ends during capture of the ctDNA, in subsequent experiments, oligonucleotide sequences complementary to the adapters are added to the ePCR product obtained. That is, the DNA single strand finally obtained is in the form of double-stranded adapters at its ends. Moreover, since there are DNA polymerase and corresponding buffer in the system, therefore in further experiments, it is to be considered whether the enzyme needs to be inactivated (generally at 65-70° C. for 10 minutes, the particular temperature being dependent on the enzyme used).

Part Two:

Single-stranded DNA is obtained in the first part. The second part involves two protocols for capturing ctDNA, as follows.

Figure 2:
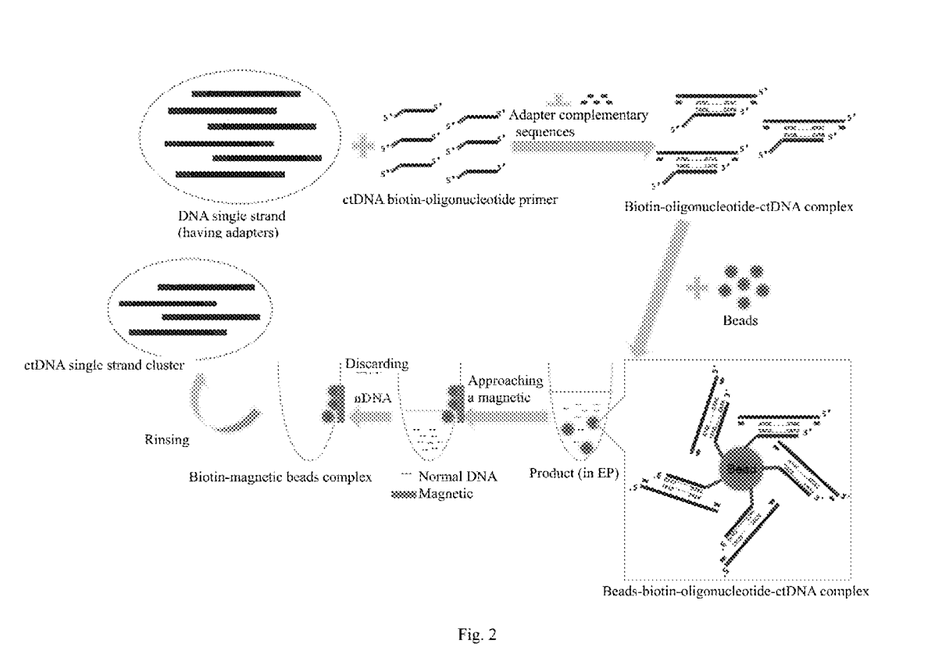
FIG. 2 is a schematic diagram showing the principle and process of capturing ctDNA by a biotin-oligonucleotide according to the present invention.

Protocol I:

With reference to FIG. 2, single-stranded ctDNA is generally captured using a magnetic bead-specific biotin-labeled oligonucleotide (biotin-oligo). The main processes of this protocol are: binding-washing-elution.

The biotin-labeled oligonucleotide comprises two portions: a gene complementary pairing portion and a biotin-labeled portion. The biotin can specifically adsorb to the surface of streptavidin magnetic beads. The ctDNA can be isolated by separating the magnetic beads, washing to remove other components, and eluting. The gene complementary pairing portion binds to the ctDNA through base complementary pairing during capture of the ctDNA.

In order to increase the efficiency of capturing the ctDNA, the length of the gene complementary pairing portion can be adjusted according to specific circumstances, and is generally around 50 bp.

Into the DNA product from the ultramicro parallel amplification, a designed biotin-labeled oligonucleotide is added. The mixture is stood at 98° C. for 5 minutes, shaken at 60° C. for 2 hours, and then cooled to room temperature. Streptavidin magnetic beads having been mixed to homogeneity and washed clean are added and shaken at room temperature for 30 minutes. The magnetic beads must be below the liquid surface to ensure sufficient binding of the beads with the ctDNA-Biotin-oligo complex containing the biotin label. Afterwards, the magnetic beads are subjected to elution. First, the reaction tube is placed on a magnetic rack for 2 minutes such that the beads are attached to the wall of the tube, and the liquid is discarded. This procedure is repeated twice such that the liquid is totally removed. Next, 300 µL of 1×B&W buffer is added to wash the beads with rapid vortexing. The tube is placed on the magnetic rack for 2 minutes such that the beads are attached to the wall of the tube, and the liquid is discarded. This procedure is repeated once. Then, 300 µL of 1×TE buffer is added to wash the beads with rapid vortexing. The tube is placed on the magnetic rack for 2 minutes such that the beads are attached to the wall of the tube, and the liquid is discarded. This procedure is repeated once. Finally, 300 µL of 0.125 M NaOH solution is added. The beads are vortexed for 1 second, then stood at room temperature for 10 minutes followed by being sufficiently vortexed. The tube is placed on the magnetic rack for 2 minutes such that the beads are attached to the wall of the tube. The supernatant is removed to obtain the captured ctDNA.

The magnetic beads can be recycled after being washed with 1×TE buffer for three times as detailed below. In the first washing, 300 µL of 1×TE buffer is added, and the beads are vortexed followed by rapid centrifugation. The tube is placed on a magnetic rack for 30 seconds such that the beads are attached to the wall of the tube, and the supernatant is discarded. In the second washing, 300 µL of 1×TE buffer (containing 0.01% Trition) is added, and the beads are vortexed followed by rapid centrifugation. The tube is placed on the magnetic rack for 30 seconds such that the beads are attached to the wall of the tube, and the supernatant is discarded. In the third washing, 300 μL of 1×TE buffer (containing 0.01% Trition) is added, and the beads are vortexed followed by rapid centrifugation. The tube is placed on the magnetic rack for 30 seconds such that the beads are attached to the wall of the tube, and the supernatant is discarded. Finally, the beads are suspended in 50 μL of 1×TE buffer (containing 0.01% Trition) for later use.

EXAMPLE 1

Blood sample of a lung cancer patient was stored in a coagulation-promoting blood-sampling tube. One (1) mL of supernatant was transferred to a 1.5 mL EP tube and centrifuged at 13,000 rpm for 1 minute. The pellet was discarded and the supernatant was saved for later use.

Four hundred (400) μL of serum was removed from the supernatant to extract DNA. The extraction was conducted using a column recovery kit (serum/plasma free DNA extraction kit available from TIANGEN). The specific procedure was as follows: (1) 40 μL of Proteinase K solution was added, and the mixture was sufficiently vortexed to homogeneity; (2) 400 μL of GB buffer and 2 μL of carrier RNA (1 ng/μL) were added, and the mixture was mixed to homogeneity and incubated at 58° C. for 10 minutes; (3) 400 μL of ethyl alcohol was added, and the mixture was stood at room temperature for 10 minutes; (4) a CR2 column was placed in a 2 mL centrifuge tube, the resulting solution was transferred to the CR2 column and centrifuged at 12,000 rpm for 30 seconds, and the waste liquid in the tube was discarded; (5) 1,000 μL of GD buffer was added, the mixture was centrifuged at 12,000 rpm for 30 seconds, and the waste liquid is discarded; (6) 1,200 μL of GD buffer was added, the mixture was centrifuged at 12,000 rpm for 30 seconds, and the waste liquid is discarded; (7) step (6) was repeated; (8) the CR2 was placed in a centrifuge and centrifuged at 12,000 rpm for 2 minutes, and then stood at room temperature for 5 minutes; and (8) the CR2 was eluted with 40 μL of TB buffer, stood at room temperature for 5 minutes, and then centrifuged at 12,000 rpm for 2 minutes. The last step could be repeated once for sufficient elution.

The extracted serum/plasma DNA was detected to have a concentration of 6.74 ng/μL.

The extracted serum/plasma DNA was subjected to ePCR, the ratio of the water phase to the oil phase being 20 μL:400 μL. The oil phase was prepared according to Formulation 3 in Table 1. One (1) mL of the oil phase comprised 700 μL of emulsifier ABIL WE90, 200 μL of paraffin oil and 730 μL of diethylhexyl carbonate.

The components dNTPs, dUTP, buffer, DNA polymerase in the water phase system were formulated into a Master Mix according to Table 2, which comprised 20 μL of 10× buffer, 5 μL of phi29 DNA polymerase (10 U/μL), 20 μL of dNTPs (10 mM), 20 μL of dUTP (0.1 mM) and 134 μL of sterilized ddH$_2$O, totaling 199 μL. One (1)μL of DNA template was added, and therefore the water phase totaled 200 μL.

Two hundred (200) μL of the water phase and 400 μL of the oil phase were sequentially added into a 1.5 mL non-stick reaction tube. The two phases were mixed, and the reaction tube was placed in a tissue lyser (Qiagen Tissue Lyser II) and shaken for 90 seconds at a parameter setting of 13 Hz. Then the 600 μL of reaction system was dispensed into 6 reaction tubes, 100 μL/tube, for conducting ePCR.

The PCR parameter settings involved a three-step procedure: the first step: pre-denaturation, 94° C., 2 min; the second step of cycling operation: denaturation 94° C., 10 sec, primer annealing, 63° C., 15 sec, elongation 72° C., 10 sec, for a total of 35 cycles; and the third step: final elongation, 72° C., 5 min. The ePCR reaction product obtained was stored at 4° C. for later use.

The ePCR reaction product obtained was subjected to post-treatment to separate the water phase from the oil phase. The specific procedure was as follows. (1) The oil phase in the upper part of the reaction tube was discarded, and 400 μL of paraffin oil was added into the reaction tube. The solution in the tube was vortexed or repeatedly pipetted until the emulsion spheres of the water phase were disrupted and the water phase and the oiled phase were sufficiently mixed. (2) The liquid mixed to homogeneity was transferred from the PCR reaction tube to a new non-stick reaction tube. The PCR reaction tube was rinsed with 400 μL of silicone oil, and the rinsed solution was added to the water phase/oil phase mixed solution. The resulting mixture was sufficiently vortexed and centrifuged at 15,000 rpm for 2 minutes, and the upper oil phase was discarded. (3) The water phase/oil phase mixed solution was rinsed using silicone oil for three times. Five hundred (500) μL of silicone oil was added, the resulting mixture was sufficiently vortexed and centrifuged at 15,000 rpm for 1 minutes, and the upper oil phase was discarded. The same procedure was repeated twice The liquid in the water phase was gently aspirated using a pipetting gun and transferred into a new EP tube, obtaining 200 μL of the PCR reaction product in the water phase.

Since there was DNA polymerase in the DNA product from the ePCR amplification, therefore before doing further experiments, the enzyme needed to be inactivated by incubating the reaction tube at 65° C. for 10 minutes.

In order to capture the ctDNA from the DNA product obtained from ePCR, a biotin-labeled oligonucleotide (Biotin-oligo) was designed. The 17$^{th}$ exon of the EGFR to be captured had the following sequence (5'-3'):

```
                                              (SEQ ID NO: 5)
GCCTAAGATCCCGTCCATCGCCACTGGGATGGTGGGGGCCCTCCTCTTGC

TGCTGGTGGTGGCCCTGGGGATCGGCCTCTTCATGCGAAGGCGCCACATC

GTTCGGAAGCGCACGCTGCGGAGGCTGCTGCAGGAGAGGGAG.
```

A gene complementary pairing portion (pairing with and binding to the portion underlined) was designed:

5'-/Bio/GAGGCCGATCCCCAGGGCCACCACCA-GCAGCAAGAGGAG GGCCCCCACCA-3'(SEQ ID NO: 6), wherein the 5'-end portion comprised the biotin label.

The oligonucleotide comprising the biotin label at the 5'-end portion was added into the DNA product from ePCR to capture the ctDNA. The specific procedure was as follows. (1) Into 200 μL of the PCR reaction product in the water phase was added 20 μL of the biotin-labeled oligonucleotide (oligonucleotide concentration 10 μM, final concentration 1 μM). The mixture was stood at 98° C. for 5 minutes, shaken at 60° C. for 2 hours, and then cooled to room temperature. (2) Fifty (50)μL of streptavidin magnetic beads having been mixed to homogeneity and washed clean were added and shaken at room temperature for 30 minutes. The magnetic beads must be below the liquid surface to ensure sufficient binding of the beads with the ctDNA-Biotin-oligo complex containing the biotin label. (3) Adsorption of the magnetic beads. The reaction tube was placed on a magnetic rack for 2 minutes such that the beads were attached to the wall of the tube, and the liquid was discarded. This procedure was repeated twice such that the liquid was totally removed. (4) Elution of the magnetic beads. Three hundred (300 μL) of 1×B&W buffer was added to wash the beads with rapid vortexing. The tube was placed on the magnetic rack for 2 minutes such that the beads were attached to the wall of the tube, and the liquid was discarded. This procedure was repeated once. Then, 300 μL of 1×TE buffer was added to wash the beads with rapid vortexing. The tube was placed on the magnetic rack for 2 minutes such that the beads were attached to the wall of the tube, and the liquid was discarded. This procedure was repeated once. Afterwards, 300 μL of 0.125 M NaOH solution was added. The beads were vortexed for 1 second, then stood at room temperature for 10 minutes followed by being sufficiently vortexed. The tube was placed on the magnetic rack for 2 minutes such that the beads were attached to the wall of the tube. The supernatant was removed to obtain the captured ctDNA.

The captured DNA product had a size of 142 bp. One (1)μL of 6× loading buffer was added to 5 μL of the capture DNA solution and sufficiently mixed to homogeneity. The resulting mixture was loaded onto agarose gel to conduct electrophoresis detection. The DNA marker used was 100 bp plus (GENSTAR), and the amount of loading was 1 μL. The agarose gel was formulated at a concentration of 2%. Two (2) g of agarose was added into 100 mL of 1×TAE buffer and heated under microwave for 2 minutes until agarose completely dissolved. When the solution cooled to 50 to 60° C., 5 μL of a nucleic acid dye (Gold View) was added, and the gel was poured.

Figure 3:
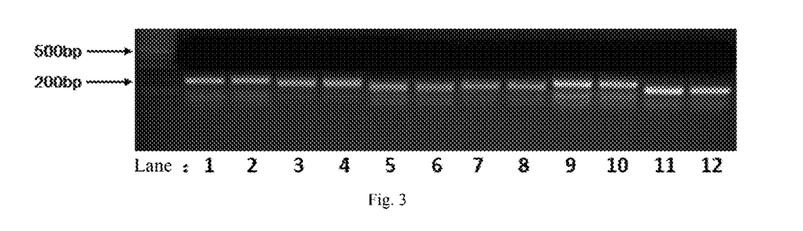
FIG. 3 is the result of gel electrophoresis detection of the ctDNA captured in Example 1 of the present invention.

The result of electrophoresis detection is as shown in FIG. 3. The captured DNA solution was loaded onto the 11$^{th}$ and 12$^{th}$ lanes. The electrophoregram indicated that the target bands were of the expected size. That is, the protocol resulted in successful capture of the ctDNA, which was useful for subsequent further detection.

Figure 4:
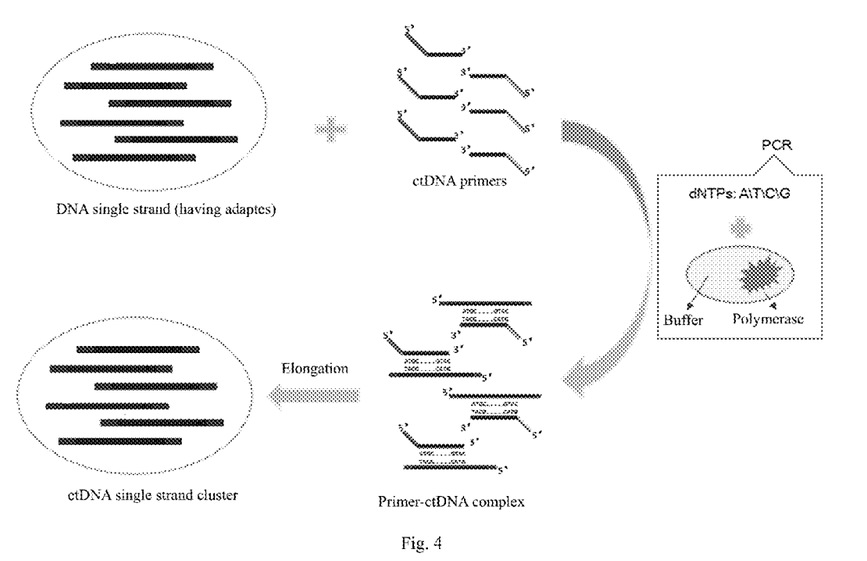
FIG. 4 is a schematic diagram showing the principle and process of capturing ctDNA by primer PCR according to the present invention.

Protocol II:

With reference to FIG. 4, ctDNA is generally obtained through primer PCR amplification. Since the DNA product from the above-said ultramicro parallel amplification comprises DNA polymerase, therefore when adopting Protocol II, the enzyme needs to be inactivated by treating at 65° C. for 10 minutes.

A PCR primers are designed, which comprise two portions: a gene complementary pairing portion and an adapter portion. The PCR primers do not need to be modified at their ends. The gene complementary pairing portion is at the 3' end, and is base paired with the single-stranded ctDNA during PCR amplification; while the adapter portion is at the 5' end and plays a role in subsequent gene sequencing.

In order to increase the efficiency of capturing the ctDNA, the length of the gene complementary pairing portion can be adjusted according to specific circumstances, and is generally around 25 bp and no shorter than 20 bp. When designing the adapter portion, its sequence is selected according to the specific sequencer used, and its length is generally no shorter than 20 bp.

As the PCR polymerase, generally selected are high-fidelity Klenow Fragment (DNA Polymerase I), KAPA HiFi family DNA polymerase, high-fidelity Phusion family DNA polymerase and high-fidelity Q5 family DNA polymerase, among others. Therefore, when designing the primer, the primer annealing temperature should be consistent with the temperature at which the polymerase selected is active.

EXAMPLE 2

Since the DNA product from the ePCR amplification in Example 1 comprised DNA polymerase, therefore before doing further experiments, the enzyme needed to be inactivated by incubating the reaction tube at 65° C. for 10 minutes.

Two hundred (200)μL of DNA product was obtained from the ePCR amplification, and the ctDNA was captured using primer PCR. PCR primers were designed. The 17$^{th}$ exon of the EGFR to be captured had the following sequence (5'-3'):

(SEQ ID NO: 5)
<u>GCCTAAGATCCCGTCCATCGCCA</u>CTGGGATGGTGGGGGCCCTCCTCTTGC

TGCTGGTGGTGGCCCTGGGGATCGGCCTCTTCATGCGAAGGCGCCACATC

GTTCGGAAGCGCACGCTGCG<u>GAGGCTGCTGCAGGAGAGGGAG</u>.

Gene complementary pairing portion (the portions underlined):

Forward primer: (5'-3')GCCTAAGATCCCGTC-CATCGCCA (SEQ ID NO: 7);

Reverse primer: (5'-3')CTCCCTCTCCTGCAGCAGC-CTC(SEQ ID NO: 8). Adapter portion (an Illumina sequencer is used):

(SEQ ID NO: 1)
Forward primer: (5'-3')TCCCTACACGACGCTCTTCCGATCT;

(SEQ ID NO: 2)
Reverse primer: (5'-3')TGAACCTGAACCGCTCTTCCGATCT.

Therefore, primers were designed as follows, wherein Tm represents annealing temperature (the salt concentration being 50 mM):

Forward Primer:

TCCCTACACGACGCTCTTCCGATCTGC-CTAAGATCCCGTCCATCGCCA (SEQ ID NO: 9, Tm: 69.7° C.); Reverse primer:

TGAACCTGAACCGCTCTTCCGATCTCTCCCTCTC-CTGCAGCAGCCTC (SEQ ID NO: 10, Tm: 68.5° C.). Two hundred (200)μL of DNA product was obtained from ePCR and was determined to be at a concentration of 50 ng/μL. One (1)μL of the product was diluted 10 folds to obtain a DNA solution at a concentration of 5 ng/μL. PCR amplification was conducted using the DNA solution at this concentration as the template.

The PCR amplification system and cycling parameters were as shown in Table 4 and Table 5. The polymerase was KAPA 2G Robust HotStart.

TABLE 4

| Proportions of components of the PCR system | | |
|---|---|---|
| Component | Final concentration | Volume |
| 2× KAPA 2G Robust HotStart ReadyMix | 1× | 50 μL |
| Forward primer (10 μM) | 0.5 μM | 5 μL |
| Reverse primer (10 μM) | 0.5 μM | 5 μL |
| Template DNA | 5 ng | 1 μL |
| PCR grade water (ddH$_2$O) | — | Making up to 100 μL |

TABLE 5

PCR cycling parameters

| Step | Temperature | Duration | Cycling times |
| --- | --- | --- | --- |
| Pre-denaturation | 95° C. | 3 min | 1 |
| Denaturation | 95° C. | 10 sec | 35 |
| Primer annealing | 63° C. | 15 sec | |
| Elongation | 72° C. | 10 sec | |
| Final elongation | 72° C. | 5 min | 1 |
| Cooling | 4° C. | Holding | 1 |

The PCR product has a size of 192 bp (including the adapters at both ends of the primers). One (1)µL of 6× loading buffer was added to 5 µL of the PCR reaction product and sufficiently mixed to homogeneity. The resulting mixture was loaded onto agarose gel to conduct electrophoresis detection. The DNA marker used was 100 bp plus (GENSTAR), and the amount of loading was 1 µL. The agarose gel was formulated at a concentration of 2% in the same manner as in Example 1.

Figure 5:
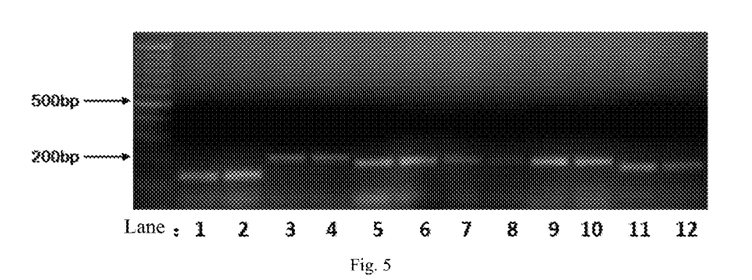
FIG. 5 is the result of gel electrophoresis detection of the ctDNA captured in Example 2 of the present invention.

The result of electrophoresis detection is as shown in FIG. 5. The captured DNA solution was loaded onto the 9$^{th}$ lane. The electrophoregram indicated that the target bands were of the expected size. That is, the protocol resulted in successful capture of the ctDNA. In order to further determine that the DNA obtained from the PCR was the 17$^{th}$ exon of EGFR, the PCR product was subjected to first-generation sequencing.

Firstly, the system was expanded to perform nucleic acid gel electrophoresis, wherein the agarose gel was formulated at a concentration of 2%, and recovery from the gel was performed. The remaining 95 µL of the PCR reaction product was sufficiently mixed with 19 µL of 6× loading buffer to homogeneity. The resulting mixture was loaded onto agarose gel to conduct electrophoresis detection. The DNA marker used was 100 bp plus (GENSTAR), and the amount of loading was 6 µL. The method of preparation of agarose gel was the same as above.

Then, the above-said PCR product was recovered from the gel (OMEGA gel recovery kit). The specific procedure was as follows. (1) The nucleic acid gel comprising the target band EGFR gene exon17 was excised under ultraviolet light, and was weighed to be 0.50000 g (the weight of the blank EP tube was 1.04100 g, and that of the excised gel added was 1.54100 g). (2) 500 µL of binding buffer XP2 was added, the mixture was incubated at 55 to 65° C. for 7 minutes until the nucleic acid gel completely dissolved, and the resulting solution was mixed to homogeneity. (3) The solution was transferred to a clean centrifuge column, the centrifuge column was placed in a new 2 mL centrifuge tube and centrifuged at 10,000 g for 1 minute, and the waste liquid was discarded. (4) The centrifuge column was added with 300 µL of binding buffer XP2 and centrifuged at 10,000 g for 1 minute, and the waste liquid was discarded. (5) The centrifuge column was added with 700 µL of wash buffer SPW and centrifuged at 13,000 g for 2 minute, and the waste liquid was discarded. (6) Step (5) was repeated. (7) The centrifuge column was placed back into the centrifuge tube and centrifuged at 13,000 g for 2 minute, and the waste liquid was discarded. (8) The centrifuge column was stood at room temperature for about 5 minutes until dry. (9) The centrifuge column was placed into a clean EP tube, and 30 µL of sterilized ddH$_2$O was added. The EP tube was stood at room temperature for 1 minute and centrifuged at 13,000 g for 1 minute. This step could be repeated once for sufficient rinsing Last, the recovered product (30 ng/µL, ≥10 µL) was submitted to Shenggong for first-generation sequencing and forward primer sequencing.

The result of sequence alignment indicated that the sequence of the PCR product aligned correctly with that of exon 17 of EGFR gene. However, the base peak diagram for the sequencing result showed that the peaks for the 1 to 50 bp DNA bases overlapped. The DNA extracted from serum included nDNA and ctDNA in a ratio of about 1,000:1. Therefore the presence of overlapped peak indicated that said part of the DNA comprised nDNA and ctDNA, and the ctDNA sequence might harbour mutations.

EXAMPLE 3

(A Life Tech Sequencer was Used):

Since the DNA product from the ePCR amplification in Example 1 comprised DNA polymerase, therefore before doing further experiments, the enzyme needed to be inactivated by incubating the reaction tube at 65° C. for 10 minutes.

DNA product was obtained from the ePCR amplification, and the ctDNA was captured using primer PCR. PCR primers were designed. The 17$^{th}$ exon of the EGFR to be captured had the following sequence (5'-3'):

```
                                              (SEQ ID NO: 5)
GCCTAAGATCCCGTCCATCGCCACTGGGATGGTGGGGGCCCTCCTCTTGC

TGCTGGTGGTGGCCCTGGGGATCGGCCTCTTCATGCGAAGGCGCCACATC

GTTCGGAAGCGCACGCTGCGGAGGCTGCTGCAGGAGAGGGAG.
```

Gene complementary pairing portion (the portions underlined):
Forward primer: (5'-3')GCCTAAGATCCCGTC-CATCGCCA (SEQ ID NO: 7); Reverse primer: (5'-3') CTCCCTCTCCTGCAGCAGCCTC(SEQ ID NO: 8). Adapter portion (a Life Tech sequencer was used):

```
                                              (SEQ ID NO: 3)
Ion_A (Red, 5'-3'):     CCATCTCATCCCTGCGTGTCTCCGA;

(SEQ ID NO: 4)
Ion_PI (Blue, 5'-3'):   CCGCTTTCCTCTCTATGGGCAGTCG.
```

Therefore, primers were designed as follows:

```
Forward primer (5'-3'):
                                             (SEQ ID NO: 11)
CCATCTCATCCCTGCGTGTCTCCGACTCAGGCCTAAGATCCCGTCCATCG

CCA;

Reverse primer (5'-3'):
                                             (SEQ ID NO: 12)
CCGCTTTCCTCTCTATGGGCAGTCGGTGATCTCCCTCTCCTGCAGCAGCC

TC.
```

Two hundred (200)µL of DNA product was obtained from ePCR and was determined to be at a concentration of 50 ng/µL. One (1)µL of the product was diluted 10 folds to obtain a DNA solution at a concentration of 5 ng/µL. PCR amplification was conducted using the DNA solution at this concentration as the template.

The PCR amplification system and cycling parameters were as shown in Table 6 and Table 7. The polymerase was Phusion DNA Polymerase.

TABLE 6

| Proportions of components of the PCR system | | |
|---|---|---|
| Component | Volumn/50 μL volumn | Final conc. |
| 5× Phusion HF Buffer | 10 μL | 1× |
| 10 mM dNTPs | 1 μL | 200 μM each |
| Forward primer | 2.5 μL | 0.5 μM |
| Reverse primer | 2.5 μL | 0.5 μM |
| Template DNA | 1 μL | 6.74 ng |
| DMSO | 1.5 μL | 3% |
| Phusion DNA Polymerase | 0.5 μL | 0.02 U/μL |
| ddH$_2$O | Making up to 50 μL | — |

TABLE 7

| PCR cycling parameters | | | |
|---|---|---|---|
| | Three-step procedure | | |
| Step of cycling | Temperature | Duration | Cycle |
| Pre-denaturation | 98° C. | 30 s | 1 |
| Denaturation | 98° C. | 5-10 s | 25-30 |
| Annealing | 63° C. | 10-30 s | |
| Elongation | 72° C. | 15-30 s/1 kb | |

TABLE 7-continued

| PCR cycling parameters | | | |
|---|---|---|---|
| | Three-step procedure | | |
| Step of cycling | Temperature | Duration | Cycle |
| Final elongation | 72° C. | 5-10 min | 1 |
| | 4° C. | Holding | |

The PCR product has a size of 192 bp (including the adapters at both ends of the primers). One (1) μL of 6× loading buffer was added to 5 μL of the PCR reaction product and sufficiently mixed to homogeneity. The resulting mixture was loaded onto agarose gel to conduct electrophoresis detection. The DNA marker used was 100 bp plus (GENSTAR), and the amount of loading was 1 μL. The agarose gel was formulated at a concentration of 2% in the same manner as in Example 1.

Figure 6:
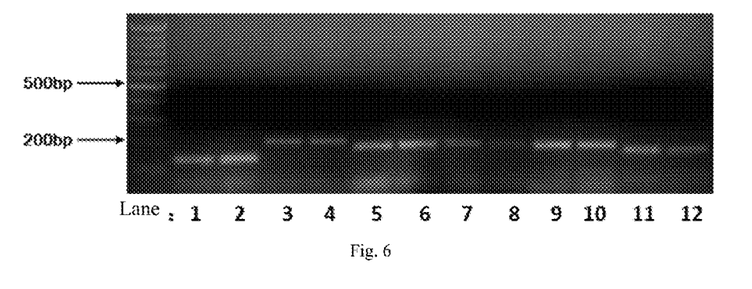
FIG. 6 is the result of gel electrophoresis detection of the ctDNA captured in Example 3 of the present invention.

The result of electrophoresis detection is as shown in FIG. 6. The captured DNA solution was loaded onto the 10$^{th}$ lane. The electrophoregram indicated that the target bands were of the expected size. That is, the protocol resulted in successful capture of the ctDNA.

The foregoing is intended to describe the present invention in further detail by way of embodiments and examples, but should not be construed as limiting the particular practice of the present invention thereto. Simple variations or modifications can be made by a person of ordinary skill in the art to which the present invention belongs without departing from the concept of the present invention.

The invention claimed is:

1. A method for enrichment of circulating tumor DNA, wherein the method comprises the steps of:

single-molecule parallel amplification: mixing a water phase and an oil phase and shaking the mixture to prepare an emulsion PCR reaction system, and performing emulsion PCR amplification, wherein the water phase comprises peripheral blood plasma DNA as template DNA, a forward primer and a reverse primer, dNTPs, a PCR buffer and a DNA polymerase, the peripheral blood plasma DNA having adapter sequences connected to both ends thereof, and the forward primer and the reverse primer being complementary to the adapter sequences at the two ends respectively; wherein the water phase of the emulsion PCR amplification component further comprises dUTP; and the dUTP and the dNTPs are in a molar ratio of from 1:1000 to 1:10;

separation of the water phase and the oil phase: separating the water phase from the oil phase following the emulsion PCR amplification to obtain a PCR amplification product in the water phase; and capture of circulating tumor DNA: capturing circulating tumor DNA in the PCR amplification product in the water phase by using a probe sequence that specifically binds to the circulating tumor DNA.

2. The method for enrichment of circulating tumor DNA of claim 1, wherein the adapter sequences are sequencing adapter sequences used in a sequencer.

3. The method for enrichment of circulating tumor DNA of claim 1, wherein the water phase and the oil phase is in a volume ratio of from 1:10 to 1:1.

4. The method for enrichment of circulating tumor DNA of claim 1, wherein the DNA polymerase is a high-fidelity DNA polymerase.

5. The method for enrichment of circulating tumor DNA of claim 1, wherein in the water phase, the peripheral blood plasma DNA is in a total amount of from 1 to 100 ng, the forward primer and the reverse primers are in a final concentration of from 0.1 to 1 µM, the dNTPs are in a final concentration of from 0.5 to 2 mM, the PCR buffer is in a final concentration of 1×, and the DNA polymerase is in a final concentration of from 0.1 to 1 U.

6. The method for enrichment of circulating tumor DNA of claim 1, wherein the probe sequence used in the step of capture of circulating tumor DNA that specifically binds to the circulating tumor DNA comprises biotin modification; after the probe sequence specifically binds to the circulating tumor DNA, the circulating tumor DNA is captured through specific binding of streptavidin magnetic beads with the biotin.

7. The method for enrichment of circulating tumor DNA of claim 1, wherein the step of capture of circulating tumor DNA is particularly achieved by performing PCR amplification using the probe sequence that specifically binds to the circulating tumor DNA as a primer, wherein the probe sequence as a primer is a sequence that specifically binds to the circulating tumor DNA.

8. A reagent for enrichment of circulating tumor DNA, wherein the reagent comprises the following components:

component for emulsion PCR amplification, which comprises a water phase and an oil phase, wherein the water phase comprises a forward primer and a reverse primer, dNTPs, a PCR buffer and a DNA polymerase, the forward primer and the reverse primer being respectively complementary to adapter sequences connected to both ends of peripheral blood plasma DNA; wherein the water phase of the emulsion PCR amplification component further comprises dUTP; and the dUTP and the dNTPs are in a molar ratio of from 1:1000 to 1:10; and component for capture of circulating tumor DNA, which comprises a probe sequence that specifically binds to the circulating tumor DNA, useful for capturing the circulating tumor DNA in the PCR amplification product in the water phase.

9. The reagent for enrichment of circulating tumor DNA of claim 8, wherein the probe sequence comprises biotin modification, and the reagent further comprises streptavidin magnetic beads, which is used to bind with the biotin to capture the circulating tumor DNA after the probe sequence specifically binds to the circulating tumor DNA.

10. The method for enrichment of circulating tumor DNA of claim 2, wherein the forward primer and the reverse primer to which the sequencing adapter sequences correspond are 5'-TCCCTACACGACGCTCTTCCGATCT-3' (SEQ ID NO: 1) and 5'-TGAACCTGAACCGCTCTTC-CGATCT-3' (SEQ ID NO: 2) respectively; or the forward primer and the reverse primer to which the sequencing adapter sequences correspond are

```
                                            (SEQ ID NO: 3)
5'-CCATCTCATCCCTGCGTGTCTCCGA-3'
and (SEQ ID NO: 4)
5'-CCGCTTTCCTCTCTATGGGCAGTCG-3' respectively.
```

11. The method for enrichment of circulating tumor DNA of claim 3, wherein the water phase and the oil phase is in a volume ratio of from 1:5 to 1:2.

12. The method for enrichment of circulating tumor DNA of claim 5, wherein in the water phase, the peripheral blood plasma DNA is in a total amount of from 1 to 10 ng, the forward primer and the reverse primers are in a final concentration of 0.5 µM, the dNTPs are in a final concentration of 1 mM, and the DNA polymerase is in a final concentration of 0.25 U.

13. The method for enrichment of circulating tumor DNA of claim 5, wherein the procedure of the emulsion PCR amplification is as follows: 93-95° C. 1-3 min; 93-95° C. 5-20 s, 61-65° C. 10-20 s, 71-73° C. 5-20 s, 40-60 cycles; and 71-73° C. 4-10 min.

14. The method for enrichment of circulating tumor DNA of claim 13, wherein the procedure of the emulsion PCR amplification is as follows: 94° C. 2 min; 94° C. 10 s, 63° C. 15 s, 72° C. 10 s, 50 cycles; and 72° C. 5 min.

15. The method for enrichment of circulating tumor DNA of claim 6, wherein in capturing the circulating tumor DNA by using the probe sequence, the adapter sequences are blocked using blocking sequences, wherein the blocking sequences specifically bind to the adapter sequences at both ends of the peripheral blood plasma DNA.

16. The reagent for enrichment of circulating tumor DNA of claim 9, wherein the dUTP and the dNTPs are in a molar ratio of 1:100.

17. The reagent for enrichment of circulating tumor DNA of claim 16, wherein the DNA polymerase is a high-fidelity Klenow Fragment, or a KAPA HiFi family high-fidelity DNA polymerase, or a Phusion family high-fidelity DNA polymerase, or a Q5 family high-fidelity DNA polymerase.

18. The reagent for enrichment of circulating tumor DNA of claim 9, wherein the reagent further comprises blocking sequences that specifically bind to the adaptor sequences at both ends of the peripheral blood plasma DNA, useful for blocking the adaptor sequences when using the probe sequence to capture the circulating tumor DNA; and the probe sequence is a sequence that specifically binds to the circulating tumor DNA, useful for performing PCR amplification to obtain enriched circulating tumor DNA.

* * * * *

SEQUENCE LISTING

<160> NUMBER OF SEQ ID NOS: 12

<210> SEQ ID NO 1
<211> LENGTH: 25
<212> TYPE: DNA
<213> ORGANISM: Artificial sequence
<220> FEATURE:
<223> OTHER INFORMATION: Synthesized sequence

<400> SEQUENCE: 1
tccctacacg acgctcttcc gatct                                    25

<210> SEQ ID NO 2
<211> LENGTH: 25
<212> TYPE: DNA
<213> ORGANISM: Artificial sequence
<220> FEATURE:
<223> OTHER INFORMATION: Synthesized sequence

<400> SEQUENCE: 2
tgaacctgaa ccgctcttcc gatct                                    25

<210> SEQ ID NO 3
<211> LENGTH: 25
<212> TYPE: DNA
<213> ORGANISM: Artificial sequence
<220> FEATURE:
<223> OTHER INFORMATION: Synthesized sequence

<400> SEQUENCE: 3
ccatctcatc cctgcgtgtc tccga                                    25

<210> SEQ ID NO 4
<211> LENGTH: 25

<212> TYPE: DNA
<213> ORGANISM: Artificial sequence
<220> FEATURE:
<223> OTHER INFORMATION: Synthesized sequence

<400> SEQUENCE: 4
ccgctttcct ctctatgggc agtcg                                         25

<210> SEQ ID NO 5
<211> LENGTH: 142
<212> TYPE: DNA
<213> ORGANISM: Homo sapiens

<400> SEQUENCE: 5
gcctaagatc ccgtccatcg ccactgggat ggtgggggcc ctcctcttgc tgctggtggt    60
ggccctgggg atcggcctct tcatgcgaag gcgccacatc gttcggaagc gcacgctgcg   120
gaggctgctg caggagaggg ag                                           142

<210> SEQ ID NO 6
<211> LENGTH: 50
<212> TYPE: DNA
<213> ORGANISM: Artificial sequence
<220> FEATURE:
<223> OTHER INFORMATION: Synthesized sequence

<400> SEQUENCE: 6
gaggccgatc cccagggcca ccaccagcag caagaggagg gcccccacca              50

<210> SEQ ID NO 7
<211> LENGTH: 23
<212> TYPE: DNA
<213> ORGANISM: Artificial sequence
<220> FEATURE:
<223> OTHER INFORMATION: Synthesized sequence

<400> SEQUENCE: 7
gcctaagatc ccgtccatcg cca                                           23

<210> SEQ ID NO 8
<211> LENGTH: 22
<212> TYPE: DNA
<213> ORGANISM: Artificial sequence
<220> FEATURE:
<223> OTHER INFORMATION: Synthesized sequence

<400> SEQUENCE: 8
ctccctctcc tgcagcagcc tc                                            22

<210> SEQ ID NO 9
<211> LENGTH: 48
<212> TYPE: DNA
<213> ORGANISM: Artificial sequence
<220> FEATURE:
<223> OTHER INFORMATION: Synthesized sequence

<400> SEQUENCE: 9
tccctacacg acgctcttcc gatctgccta agatcccgtc catcgcca                48

<210> SEQ ID NO 10
<211> LENGTH: 47
<212> TYPE: DNA
<213> ORGANISM: Artificial sequence
<220> FEATURE:
<223> OTHER INFORMATION: Synthesized sequence

```
<400> SEQUENCE: 10
tgaacctgaa ccgctcttcc gatctctccc tctcctgcag cagcctc                47

<210> SEQ ID NO 11
<211> LENGTH: 53
<212> TYPE: DNA
<213> ORGANISM: Artificial sequence
<220> FEATURE:
<223> OTHER INFORMATION: Synthesized sequence

<400> SEQUENCE: 11
ccatctcatc cctgcgtgtc tccgactcag gcctaagatc ccgtccatcg cca          53

<210> SEQ ID NO 12
<211> LENGTH: 52
<212> TYPE: DNA
<213> ORGANISM: Artificial sequence
<220> FEATURE:
<223> OTHER INFORMATION: Synthesized sequence

<400> SEQUENCE: 12
ccgctttcct ctctatgggc agtcggtgat ctccctctcc tgcagcagcc tc           52
```